United States Patent [19]

Hasson

[11] Patent Number: 5,037,430
[45] Date of Patent: Aug. 6, 1991

[54] CLAMP FOR GYNECOLOGICAL INSTRUMENTS

[76] Inventor: Harrith M. Hasson, 2043 N. Sedgwick, Chicago, Ill. 60614

[21] Appl. No.: 75,238

[22] Filed: Jul. 17, 1987

Related U.S. Application Data

[63] Continuation of Ser. No. 816,325, Jan. 6, 1986.

[51] Int. Cl.⁵ .............................................. A61B 17/44
[52] U.S. Cl. ...................................... 606/119; 606/208
[58] Field of Search ................................ 128/321–323, 128/303 R, 346, 348.1, 912, DIG. 26; 604/174, 178, 210, 55, 324; 81/300, 376, 377; 433/4; 606/205–209, 119

[56] References Cited

U.S. PATENT DOCUMENTS

| 75,693 | 3/1868 | Morrell . | |
|---|---|---|---|
| 1,683,384 | 9/1928 | Durham, Jr. | 279/79 |
| 2,601,613 | 6/1952 | Gladstone . | |
| 2,662,524 | 12/1953 | Hudgins | 604/174 |
| 3,019,790 | 2/1962 | Militana | 128/322 |
| 3,085,339 | 4/1963 | Wolfe | 433/4 |
| 3,948,270 | 4/1976 | Hasson . | |
| 4,000,743 | 1/1977 | Weaver | 128/DIG. 26 |
| 4,083,369 | 4/1978 | Sinnreich . | |
| 4,192,313 | 3/1980 | Ogami . | |
| 4,300,564 | 11/1981 | Furihata | 128/321 |
| 4,430,076 | 2/1984 | Harris . | |
| 4,432,352 | 2/1984 | Wineland | 128/321 |
| 4,489,732 | 12/1984 | Hasson . | |
| 4,496,345 | 1/1985 | Hasson . | |
| 4,559,944 | 12/1985 | Jaeger | 128/321 |

Primary Examiner—C. Fred Rosenbaum
Assistant Examiner—Sharon Rose
Attorney, Agent, or Firm—Wood, Phillips, Mason, Recktenwald & VanSanten

[57] ABSTRACT

A clamping device for positioning and holding gynecological instruments, such as uterine instruments, or the like. The device is illustrated in the form of a forceps having handles located at one end, and clamps located at the opposite end for selectively clamping onto at least a portion of the cervix. A second clamp is located intermediate the ends of the forceps for releasably clamping onto the gynecological instrument to hold the instrument in proper position relative to the uterus.

2 Claims, 1 Drawing Sheet

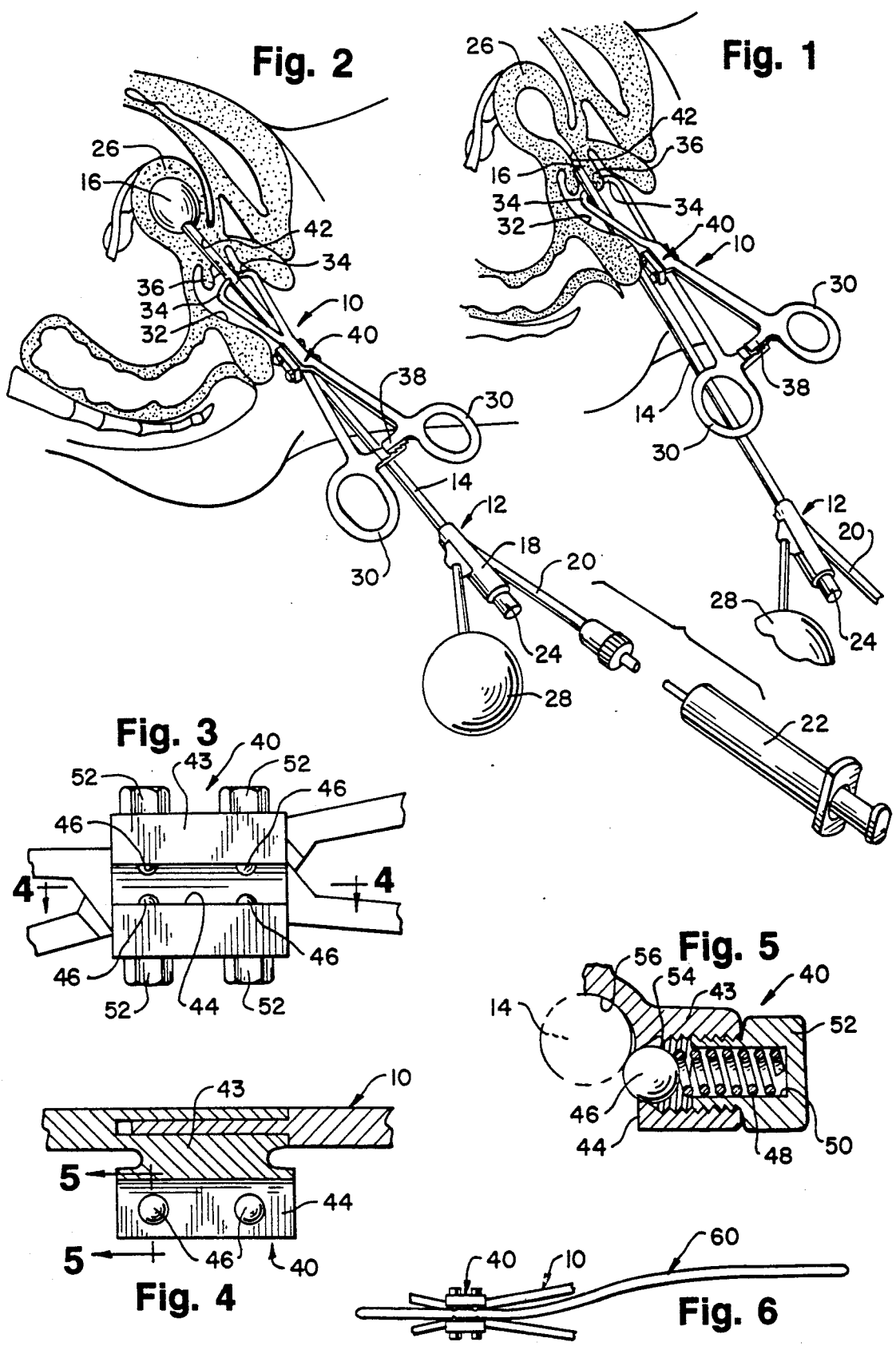

CLAMP FOR GYNECOLOGICAL INSTRUMENTS

This application is a continuation of application Ser. No. 816,325, filed Jan. 6, 1986.

FIELD OF THE INVENTION

This invention relates to a gynecological instrument and, more particularly, to a clamping device that may be advantageously employed for positioning and holding gynecological instruments, such as uterine instruments, or the like.

BACKGROUND OF THE INVENTION

There are a variety of medical implements in the form of uterine instruments for measuring, elevating and otherwise manipulating the uterus. For instance, a uterine instrument is shown in my U.S. Pat. No. 4,496,345 which issued on Jan. 29, 1985. In that patent, as well as my U.S. Pat. No. 3,948,270, I disclose a novel uterine cannula which is useful in a variety of gynecological procedures wherein uterine elevation or manipulation and/or uterotubal injection are indicated. Reference may be had to those patents for specific identification of the nature and types of such procedures.

Another type of intrauterine instrument includes adjustable uterine dilators or sets of dilators.

With gynecological instruments used to elevate or manipulate the uterus, as described above, there is always the potential problem that elevating the uterus with the intrauterine instrument might cause perforation of the uterine fundus or damage to the uterine wall if the force of elevation is excessive. As the instrument pushes up on the fundus, it may tent or perforate the fundus. It can be understood that this may create problems when using intrauterine instruments as described above.

There is a need for a device or means by which the use of intrauterine instruments can be made easier and safer and the problems described above solved by simple means.

SUMMARY OF THE INVENTION

An object, therefore, of the invention is to provide a clamping device for facilitating positioning and holding gynecological instruments, such as uterine instruments, or the like.

In the exemplary embodiment of the invention, the device generally is in the form of a forceps having handle means at one end for inserting the device into the vaginal canal, forceps clamp means at the opposite end for selectively clamping onto at least a portion of the cervix, and second clamp means intermediate the ends of the forceps for releasably clamping onto the gynecological instrument to hold the instrument in proper position relative to the uterus. The forceps is illustrated herein generally in the form of a tenaculum forceps.

Preferably, the second clamp means include means for releasably clamping an elongated or tubular instrument, such as a uterine probe, a uterine dilator, a ballooned cannula or the like and preventing the elongated instrument from pivoting. Specifically, the clamp means includes an elongated channel for receiving the elongated instrument or a portion thereof. Longitudinally spaced, spring loaded balls are mounted within the channel for holding the instrument therewithin. The clamp means preferably is located at the joint of the forceps and can thereby be easily snapped onto the elongated portion of the gynecological instrument after the instrument has been properly positioned. The combined device (composed of the clamping device and the elevating instrument) thereby can support, elevate and rotate the uterus while preventing the elevating instrument from further movement within the uterus.

Other objects, features and advantages of the invention will be apparent from the following detailed description taken in connection with the accompanying drawings.

DESCRIPTION OF THE DRAWINGS

The features of this invention which are believed to be novel are set forth with particularity in the appended claims. The invention, together with its objects and the advantages thereof, may be best understood by reference to the following description taken in conjunction with the accompanying drawings, in which like reference numerals identify like elements in the figures and in which:

FIG. 1 is a somewhat diagrammatic view illustrating a clamping device made according to the invention disposed within the vagina and clamping the cervix of a patient, and with a ballooned cannula in the process of being inserted into the uterus of the patient;

FIG. 2 is a view similar to that of FIG. 1, with the ballooned cannula fully inserted, inflated to provide uterine elevation, and clamped to the clamping device of the invention;

FIG. 3 is a fragmented, bottom plan view, on an enlarged scale, of the clamp means for the cannula;

FIG. 4 is a fragmented vertical section, on an enlarged scale, taken generally along line 4-4 of FIG. 3;

FIG. 5 is a fragmented vertical section, on a further enlarged scale, taken generally along line 5-5 of FIG. 4; and FIG. 6 is a reduced view similar to that of FIG. 3, with a uterine dilator being clamped by the device of the invention.

DETAILED DESCRIPTION OF THE PREFERRED EMBODIMENT

Referring to the drawings in greater detail, and first to FIGS. 1 and 2, the invention contemplates a clamping device, generally designated 10, for positioning and holding gynecological instruments, such as uterine instruments or the like. An exemplary embodiment of a uterine instrument in the form of a ballooned cannula, generally designated 12, is illustrated herein for use with clamping device 10. However, it should be understood that the invention is equally applicable for use with other uterine instruments, such as uterine dilators, uterine measuring probes, or other gynecological instruments.

Cannula 12 includes an elongated shaft 14 terminating in a balloon tip 16. The end of shaft 14 opposite balloon tip 16 is provided with a handle 18 whereby the entire cannula may be manipulated. One part of handle 18 includes a pressure air or fluid entrance 20 which is adapted to be associated with a syringe 22 or the like. Introduction of air or fluid by syringe 22 is operable to expand balloon 16.

Handle 18 of cannula 12 also includes an injection receiver 24 which may be associated with a suitable syringe (not shown) whereby fluid may be injected through the shaft 14 into the interior of a body cavity as, for example, a uterus 26. Handle 18 also may removably receive a weight 28 which serves to elevate uterus 26 when the cannula is properly disposed therein. Weight 28 also serves to cause the expanded balloon 16 (FIG. 2) to seal the uterus and prevent retrograde leakage of the injected fluid or air.

Clamping device 10 is illustrated generally in the form of a forceps, particularly in the form of a tenaculum forceps. The device includes finger and thumb handle means 30 at one end for inserting the device into the vaginal canal 32. First, pointed clamp means 34 are provided at the opposite end of forceps 10 for insertion through vaginal canal 32 and for selectively clamping onto at least a portion of a cervix 36, preferably the upper portion of the cervix as illustrated in FIG. 2. As is known, ratcheted lock tabs 38 hold forceps 10 in clamped condition.

Second clamp means, generally designated 40, are provided on forceps 10 and, preferably, located at the joint of the forceps as illustrated in FIGS. 1 and 2. Clamp means 40 is designed for releasably clamping onto a gynecological instrument, such as cannula 12, to hold the instrument in proper position within uterus 26 as clamps 34 clamp onto cervix 36.

In use, the cervix 36 is exposed and grasped by first clamp means 34 of forceps 10 to hold the cervix and expose the entrance to cervical canal 42. Appropriate uterine dimensions may then be determined utilizing a sound as is known in the art. Cannula 12, with balloon tip 16 deflated, then is inserted through cervical canal 42 into uterus 26 until the uterine fundus is touched. The balloon may be backed up slightly and then inflated, normally with air, by means of syringe 22. Once balloon 16 is inflated, the inflation syringe is removed and withdrawal of the cannula from the uterine cavity is gently attempted. Resistance to such withdrawal confirms that the balloon is properly inflated Shaft 14 of cannula 12 then is clamped by clamp means 40 on forceps 10, thereby fixing the relationships between forceps 10, cannula 12, cervix 36 and uterus 26 and preventing cannula 12 from further movement within uterus 26. In this manner, the uterus can be elevated or rotated at will without the least possibility of uterine perforation. When the procedure is completed, shaft 14 simply is released from clamp means 40 and manipulated and/or removed from the uterus as required.

From the foregoing, it can be seen that clamping device or forceps 10 initially stabilizes a uterus for subsequent insertion of the balloon tipped cannula 12 and thereafter clamps on cannula 12 thereby fixing cannula 12 to the cervix and preventing cannula 12 from moving further into the uterine cavity.

The specifics of clamp means 40 are illustrated in FIGS. 3-5. More particularly, clamp means 40 are located at the pivot joint of forceps 10 as described in relation to FIGS. 1 and 2. The clamp means includes a block or body 43 defining an elongated channel 44 which extends front-to-rear of the forceps for receiving an elongated instrument, such as shaft 14 of cannula 12. The elongation of the channel prevents pivoting of the elongated instrument in a transverse plane through the channel. Four detent balls 46 are provided in two longitudinally spaced pairs thereof inside channel 44. The detent balls of each longitudinally spaced pairs thereof face each other as best illustrated in FIG. 3. As seen in FIG. 5, each detent ball 46 is spring loaded by means of a compression coil spring 48 disposed within a socket 50 of a bolt 52 threaded into block 43. Each detent ball seats against an interior socket 54 and can move into block 43 out of the bounds of channel 44. The base of channel 44 is rounded, as at 56 in FIG. 5, to define an elongated receptacle for shaft 14 of cannula 12 as spring-loaded detent balls 46 hold the elongated shaft in clamp means 40. Four detent balls 46 (i.e. two longitudinally spaced pairs) are provided to prevent pivoting of elongated shaft 14 in a plane which includes the opening to channel 44.

It can be seen that while the detent balls clamp and position an instrument, such as cannula 12, the detent balls afford relative rotation between the instrument relative to forceps 10 about a longitudinal axis such as defined by shaft 14. In other words, the instrument can rotate relative to the forceps without rotating the uterus, or the forceps itself can rotate the entire uterus or both can be rotated simultaneously.

FIG. 6 shows clamp means 40 releasably clamping another type of gynecological instrument, such as a uterine dilator, generally designated 60. It should be understood that the clamping device of this invention is not limited solely to the use of cannula 12, and the cannula is illustrated herein for describing a use and not any limitations of the invention.

It will be understood that the invention may be embodied in other specific forms without departing from the spirit or central characteristics thereof. The present examples and embodiments, therefore, are to be considered in all respects as illustrative and not restrictive, and the invention is not to be limited to the details given herein.

I claim:

1. Clamping means for positioning and holding gynecological instruments, comprising:
   a mounting device adapted for vaginal insertion and defining a joint, a proximal end and a distal end;
   a handle on said proximal end of the device for controlling the insertion of the device into a vaginal canal to dispose said distal end thereof adjacent the cervix;
   a first clamp on said distal end of the device and operative in response to manipulation of the handle to adjustably clamp onto at least a portion of the cervix; and
   a second clamp for releasably clamping a gynecological instrument to an intermediate portion of the device between said proximal and distal ends to hold the instrument in a preselected position relative to the first clamp handle in the uterus independently of the clamping configuration of the fist clamp, said second clamp being fixedly associated with the device adjacent said joint, said clamping means comprising means for firstly clamping the cervix by the first clamp and permitting a gynecological instrument to be subsequently inserted into the uterus and clamped and held by the second clamp in a preselected position relative to the cervix,
   wherein the second clamp includes an elongated channel for receiving the elongated instrument and longitudinally spaced retaining means for holding the instrument in the channel,
   wherein said retaining means comprises spring loaded balls.

2. Clamping means for positioning and holding gynecological instruments, comprising:
   a mounting device adapted for vaginal insertion and defining a joint, a proximal end and a distal end;
   a handle on said proximal end of the device for controlling the insertion of the device into a vaginal canal to dispose said distal end thereof adjacent the cervix;

a first clamp on said distal end of the device and operative in response to manipulation of the handle to adjustably clamp onto at least a portion of the cervix; and a second clamp for releasably clamping a gynecological instrument to an intermediate portion of the device between said proximal and distal ends to hold the instrument in a preselected position relative to the first clamp handle in the uterus independently of the clamping configuration of the fist clamp, said second clamp being fixedly associated with the device adjacent said joint, said clamping means comprising means for firstly clamping the cervix by the first clamp and permitting a gynecological instrument to be subsequently inserted into the uterus and clamped and held by the second clamp in a preselected position relative to the cervix, wherein the second clamp includes a longitudinal slot, with four spring loaded balls adapted to engage the instrument disposed therein, said balls being positioned in pairs opposite one another with the two pairs being longitudinally spaced.

* * * * *